United States Patent [19]

McKinzie et al.

[11] Patent Number: 5,529,770
[45] Date of Patent: Jun. 25, 1996

[54] VISCOUS LIQUID CONDITIONING TOPICAL GERMICIDES

[75] Inventors: Michael D. McKinzie, Kansas City, Mo.; Elizabeth L. Lenahan, Olathe, Kans.; Thomas C. Hemling, Lake Winnebago, Mo.

[73] Assignee: West Agro, Inc., Kansas City, Mo.

[21] Appl. No.: 353,445

[22] Filed: Dec. 9, 1994

[51] Int. Cl.$^6$ ............ A61K 31/78; A61K 33/36; A61K 31/155; A61K 31/08; A61K 31/045; A61K 47/00

[52] U.S. Cl. ............ 424/78.24; 424/78.25; 424/667; 424/668; 514/635; 514/781; 514/723; 514/738

[58] Field of Search ............ 424/667, 668, 424/78.24, 78.25; 514/635, 781, 738, 723

[56] References Cited

U.S. PATENT DOCUMENTS

| | | | |
|---|---|---|---|
| 4,199,564 | 4/1980 | Silver et al. | 424/80 |
| 4,376,787 | 3/1983 | Lentsch et al. | 424/315 |
| 4,434,181 | 2/1984 | Marks, Sr. et al. | 424/326 |
| 4,891,216 | 1/1990 | Kross et al. | 424/78 |
| 5,017,369 | 5/1991 | Marhevka | 424/78 |
| 5,063,249 | 11/1991 | Andrews | 514/673 |
| 5,211,961 | 5/1993 | Adkinson | 424/616 |
| 5,330,768 | 7/1994 | Park et al. | 424/501 |

FOREIGN PATENT DOCUMENTS

| | | |
|---|---|---|
| 0487066 | 11/1991 | European Pat. Off. . |
| 8900006 | 1/1989 | WIPO . |

OTHER PUBLICATIONS

Boikova, et al.; CA Selects:Antibacterial Agents, No. 117: 14297y; Issue 15, 1992.

1994 Functional Materials/North American, p. 294; Theothik 80-11.

An Introduction to Methocel Cellulose Ethers, 1994.

West Agro, inc.; Raw Material Specifications; Keltrol (Xanthan Gum); Nov. 19, 1984.

West Agro, Inc.; Raw Material Specifications; Pluornic P-105 (Poloxamer 335); Feb. 15, 1993.

West Agro, Inc.; Raw Material Specifications; Nonoxynol 12; Feb. 4, 1992.

West Agro, Inc. Raw Material Specifications; Sodium Iodide-Iodine Complex; Dec. 16, 1992.

Product Data; Natrosol 250, No. 401-8, Hercules Incorporated, 1994.

Cytec Material Safety Data; Aerosol OT 75% Surfactant; May 16, 1994.

West Agro, Inc.; Raw Material Specifications; Pluoronic P-123W (Poloxamer 403); Jun. 7, 1993.

CA 79:35145, Cantor et al., 1973.

*Primary Examiner*—Kimberly Jordan
*Attorney, Agent, or Firm*—Hovey, Williams, Timmons & Collins

[57] ABSTRACT

Improved, highly viscous film-forming protective germicidal formulations are provided which include water, a germicidal agent (preferably complexed iodine) together with an organic thickener, a skin conditioning agent and a minor amount of polyvinyl pyrrolidone. Preferably, the formulations include iodine complexed with a Poloxamer and PVP, in combination with a xanthan gum and glycerin. The formulations have a viscosity of from about 50–5000 cP and form a flexible residual film when applied to skin. The invention is particularly useful in the preparation of bovine teat dips.

22 Claims, No Drawings

VISCOUS LIQUID CONDITIONING TOPICAL GERMICIDES

BACKGROUND OF THE INVENTION

1. Field of the Invention

The present invention is broadly concerned with viscous germicidal topical skin treatments which provide a residual protective film of conditioning agents upon application thereof, to thereby counteract the potentially irritating effects of the germicidal agent. More particularly, the invention pertains to such formulations which include a germicidal agent such as iodine, in combination with a thickener and polyvinyl pyrrolidone; the compositions have a viscosity of from about 50–5000 cP and are characterized by leaving a residual protective and conditioning film when applied to skin. In preferred embodiments, improved teat dip products are provided in accordance with the invention.

2. Description of the Prior Art

Iodine sanitizing solutions are widely used as topical skin antiseptic agents (e.g., as teat dips) for germicidal purposes. In the case of teat dips, control of mastitis in lactating cows is a primary consideration. Iodine germicides are generally liquid and of low viscosity (1–20 cP), and provide only a minimal amount of residual solution on skin. Iodine teat dips of this type normally contain from about 0.1–1% available iodine on a nominal basis, and may also contain various conditioning agents such as glycerin or the like. Conditioning agents are provided in iodine germicidal products in order to ameliorate the potentially harmful effects of the iodine germicidal agent.

In the past, several teat dip products have been marketed as "barrier" teat dips. These products are said to provide a barrier film that remains on the teats between milkings, and are claimed to provide protection from environmental bacteria and harsh weather conditions. There is little proof that these formulations actually provide a true barrier function. The residual films provided by these prior products contain organic polymers, surfactants and germicides and are often low in pH. Many of these formulas include ingredients which could be considered irritating to the skin, and several contain large concentrations of volatile alcohols which are known to have a drying or dehydrating effect on skin.

U.S. Pat. No. 5,063,249 describes teat dips comprising a dodecylaminoalkylamine derivative, an emollient and PVP as a film-forming agent. However, it is believed that the dips described in this reference are very fluid and non-viscous.

U.S. Pat. No. 4,199,564 describes film-forming teat dips including water soluble lower alkanol biocides, a film-forming polymer and an emollient.

There is accordingly an unsatisfied need in the art for an improved teat dip having a relatively high viscosity providing significant film-forming capability and resultant protective properties; products in accordance with the invention contain maximum amounts of conditioning agent in the resultant film, so as to provide the most effective skin protection.

SUMMARY OF THE INVENTION

The present invention overcomes the problems outlined above, and provides germicidal products having viscosities in the range of from about 50–5000 cP which are characterized by the property of leaving a protective residual film on skin. Broadly speaking, the formulations of the invention are in the form of aqueous compositions including therein a germicidal agent, a thickener and a minor amount of polyvinyl pyrrolidone. The preferred teat dips in accordance with the invention contain a germicidal agent such as iodine which is effective for the prevention of bovine mastitis.

More particularly, the preferred teat dips hereof have a germicidal agent selected from the group consisting of iodine and chlorhexidine, with the most preferred agent being complexed iodine. In the latter case, it is preferred that the weight ratio of complexing agent to iodine be from about 2.0:1 to 4.5:1, but such formulations may require careful selection of complexing agent to achieve a weight ratio within this range. The thickener component is preferably selected from the group consisting of cellulose, cellulose derivatives and gums. The PVP ingredient should preferably have a molecular weight of from about 10,000–150,000, and more preferably from about 25,000–90,000. The skin conditioning agent is usually glycerin, although other emollients and conditioners can be employed.

If desired, other ingredients such as sources of iodate ion, buffering agents, wetting agents and dyes can be added to the teat dip formulations of the invention.

DETAILED DESCRIPTION OF THE PREFERRED EMBODIMENTS

The singlemost preferred germicidal agent used in the formulations hereof is in the form of complexed iodine, with an average available (titratable) iodine level of from about 0.1–2% by weight on a nominal basis, and more preferably from about 0.25–1% by weight. In some instances, a given formulation such as a teat dip may have a nominal available iodine of 1%, but in fact the formulation may contain as much as 1.2% or even 1.25% by weight available iodine. This occurs because most compositions will contain an "overage" of available iodine when manufactured, so as to allow for iodine loss over the life of the product. As such, it will be understood that reference herein to average available iodine on a nominal basis covers such excess amounts.

The complexed iodine of the invention is preferably prepared through the use of iodine and complexing agent selected from the group consisting of ethoxylated surfactants, cellulose, cellulose derivatives and the polyvinyl pyrrolidone component. The alkoxylated (usually ethoxylated) surfactants include, but are not limited to, the group consisting of alkylphenol ethoxylates, ethoxylated fatty acids, alcohol ethoxylates, alcohol alkoxylates, polysorbates (ethoxylated sorbitol) and ethylene oxide-propylene oxide copolymers (Poloxamers). The most preferred Poloxamer surfactants are those described in U.S. Pat. No. 5,368,868, which is incorporated by reference herein. These surfactants include a polyoxypropylene moiety having an average molecular weight in excess of 2600, and more preferably from about 2600–4000. The polyoxyethylene content typically ranges from about 30–75% by weight, and more preferably from about 40–70% by weight. Generally speaking, the complexing agents would be used at a level of from about 0.4–10% by weight, and more preferably from about 0.4–4% by weight. However, because of their efficiency in complexing iodine, the preferred Poloxamers can be used at relatively low concentrations. This in turn gives a residual film which is less irritating and can contain a higher percentage of the desired conditioning agent. Moreover, because of their waxy nature, the preferred Poloxamer surfactants assist in formation of a film that is soft, waxy and more resistant to abrasion than prior rigid films.

The polyvinyl pyrrolidone component is preferably taken from the group of K-30 through K-90 povidones. The PVP primarily serves as a film forming agent but also may serve in part as an iodine complexing agent, and indeed can be used for this purpose. However, PVP is normally used at relatively low levels because of its high cost as compared with other complexors. Levels of use are typically from about 0.5–5% by weight PVP, and more preferably from about 1.0–2.5% by weight. When iodine is used as the germicidal agent, the PVP can serve two functions, i.e., as a film former and as an iodine complexor. However, at PVP:$I_2$ weight ratios of less than about 2:1, an auxiliary complexing agent is normally required. When mixtures of PVP and Poloxamer are used, the amount of Poloxamer required is extremely low, which further reduces potential for irritation. The film forming characteristics of PVP can be dependent upon other ingredients in a given formulation. For example, in the absence of an ethoxylated surfactant, the resultant PVP film is dryer and more subject to removal by abrasion than films containing both PVP and an ethoxylated surfactant.

The thickeners useful in the context of the invention are preferably taken from the group consisting of alkyl celluloses, the alkoxy celluloses, xanthan gum, guar gum, polyorgano sulfonic acid and mixtures thereof. The thickeners are chosen based on compatibility with the other formulation ingredients and desired viscosity. Generally speaking, the thickener should be present at a level of from about 0.05–10% by weight, and more preferably from about 0.1–1% by weight.

The skin conditioning agents are incorporated into the products of the invention to provide healing and to protect skin from irritation and chapping. This is particularly the case with teat dips where teat skin can be adversely affected by harsh weather and/or treatment (e.g., milking three times per day). The useful conditioning agents are preferably selected from the group consisting of glycerin, propylene glycol, sorbitol, lanolin, lanolin derivatives, acyl lactylates, polyethylene glycol, aloe vera, allantoine, alginates, monoester salts of sulfosuccinates, alphahydroxy fatty acids, esters of fatty acids, ceramides, and mixtures thereof. Broadly, the conditioning agents are used at a level of from about 0.5–20% by weight. The most preferred conditioning agents are glycerin and/or propylene glycol, and are usually employed at a level of from about 1–20% by weight, and more preferably from about 2–10% by weight. It has also been found that certain conditioning agents can modify the nature of the barrier film. Certain high molecular weight polyethylene glycols for example can be used to give the resultant films a waxy nature.

The products of the invention are formulated so as to achieve final viscosities of from about 50–5000 cP (Brookfield viscosity measured using Spindle #2 at 6 rpm). More preferably, the viscosity of the dips is from about 100–2500 cP, and most preferably from about 100–1000 cP.

Various optional ingredients may be provided with the formulations of the invention. For example, iodate ion, buffers, dyes and wetting agents can be employed as desired. The most preferred buffering agent are the citrate salts, e.g., sodium citrate.

The following examples describe illustrative film-forming teat dips in accordance with the invention, and comparisons with conventional dips. It is to be understood that these examples are provided by way of illustration only, and nothing therein should be taken as a limitation upon the overall scope of the invention.

EXAMPLE 1

A series of teat dip formulations were prepared in accordance with the invention. In each case, the following mixing procedure was followed.

1. Methocel E4M Premium, Methocel E10M Premi um, Rheothik 80-11, and/or Keltrol (where applicable) are dispersed in glycerin and/or propylene glycol.

2. The dispersions of step 1, together with Pluronic P-105, Pluronic P-123, or Igepal CO-720 (where applicable), citric acid, and Aerosol OT-75 are dispersed with stirring into 60% by weight of the formula amount of water at a temperature of 140°–165° F.

3. The PVP K-30 or K-90 is stirred into the mixture of step 2 until the PVP is dissolved.

4. Add 30% or 35% of the formula amount of cold water (see step 7) and stir until the product temperature falls to 100° F. or less.

5. The sodium iodide-iodine complex, or the TDC-20 complex, is added with stirring until dissolved.

6. Sodium hydroxide is added to adjust the pH of the product to a desired level, between pH 4–6.

7. If the formula requires sodium iodate, this material is mixed in 5% of the formula amount of water and the result is added to the mixture of step 6 with stirring.

The following table sets forth the ingredients of each teat dip composition, as well as the viscosity recorded for each composition. All of the compositions were suitable for use as teat dips. Films provided by the described formulations were evaluated in the following manner. A 16 mm diameter glass culture tube was immersed in the composition to a depth of 6½ to 7 cm and allowed to dry in air for about 4 hours. The resultant film was then examined visually as well as by touch.

TABLE 1

| Ingredient | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| PVP, K-90 | 2.0 | 2.0 | 2.0 | 2.0 | 2.0 | 2.0 | — | — | — | — | — | — | — | — |
| PVP, K-30 | — | — | — | — | — | — | 2.0 | 2.0 | 2.0 | 2.0 | 2.0 | 2.0 | 2.0 | 2.0 |
| Pluronic P-105 | 0.50 | 0.5 | 0.5 | 2.0 | 2.0 | 2.0 | 2.0 | 2.0 | 2.0 | 0.5 | 0.5 | 2.0 | 2.0 | 2.0 |
| Igepal CO-720 | — | — | — | — | — | — | — | — | — | — | — | — | — | — |
| Pluronic P-123 | — | — | — | — | — | — | — | — | — | — | — | — | — | — |
| NaI-$I_2$ Complex | 1.75 | 1.75 | 1.75 | 1.75 | 1.75 | 1.75 | 1.75 | 1.75 | 1.75 | 1.75 | 1.75 | 1.75 | 1.75 | 1.75 |
| TDC-20 Complex | — | — | — | — | — | — | — | — | — | — | — | — | — | — |

TABLE 1-continued

| Ingredient | | | | | | | | | | | | | | |
|---|---|---|---|---|---|---|---|---|---|---|---|---|---|---|
| Sodium Iodate | 0.3 | 0.3 | 0.3 | 0.3 | 0.3 | 0.3 | 0.3 | 0.3 | 0.3 | 0.3 | 0.3 | 0.3 | 0.3 | 0.3 |
| Citric Acid | 0.25 | 0.25 | 0.25 | 0.25 | 0.25 | 0.25 | 0.25 | 0.25 | 0.25 | 0.25 | 0.25 | 0.25 | 0.25 | 0.25 |
| Aerosol OT-75 | 0.05 | 0.05 | 0.05 | 0.05 | 0.05 | 0.05 | 0.05 | 0.05 | 0.05 | 0.05 | 0.05 | 0.05 | 0.05 | 0.05 |
| Sodium Hydroxide | 0.1 | 0.1 | 0.1 | 0.1 | 0.1 | 0.1 | 0.1 | 0.1 | 0.1 | 0.1 | 0.1 | 0.1 | 0.1 | 0.1 |
| Methocel E4M Premium | — | — | — | 0.2 | 0.2 | 0.2 | 0.2 | 0.2 | 0.1 | 0.2 | 0.1 | — | — | — |
| Methocel E10M Premium | 0.1 | 0.1 | 0.1 | — | — | — | — | — | — | — | — | — | — | — |
| Rheothik 80-11 | — | — | — | — | — | — | — | — | — | — | — | — | — | — |
| Keltrol | 0.2 | 0.2 | 0.2 | 0.2 | 0.2 | 0.2 | 0.2 | 0.1 | 0.2 | 0.1 | 0.2 | 0.1 | 0.1 | 0.2 |
| Glycerin | — | 5.0 | 10.0 | — | 5.0 | 10.0 | 5.0 | 10.0 | 10.0 | 10.0 | 10.0 | — | 10.0 | — |
| Propylene Glycol | 10.0 | 5.0 | — | 10.0 | 5.0 | — | 5.0 | — | — | — | — | 10.0 | — | 10.0 |
| Water | q.s. | q.s. | q.s. | q.s. | q.s. | q.s. | q.s. | q.s. | q.s. | q.s. | q.s. | q.s. | q.s. | q.s. |
| Brookfield Viscosity (CP, Spindle #2, 6 RPM) | 375 | 400 | 500 | 175 | 175 | 200 | 600 | 162 | 500 | 150 | 540 | 125 | 125 | 450 |

| Ingredient | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|
| PVP, K-90 | — | — | — | — | — | — | — | — | — | — | — | — | — | — | — |
| PVP, K-30 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| Pluronic P-105 | 2.0 | 0.5 | 0.5 | 0.5 | 0.5 | 2.0 | 2.0 | 0.5 | 1.0 | 0.5 | 2.0 | 2.0 | — | — | 2.0 |
| Igepal CO-720 | — | — | — | — | — | — | — | — | — | — | — | — | — | 6.0 | — |
| Pluronic P-123 | — | — | — | — | — | — | — | — | — | — | — | — | 2.0 | — | — |
| NaI-$I_2$ Complex | 1.75 | 1.75 | 1.75 | 1.75 | 1.75 | 1.75 | 1.75 | 0.44 | 0.44 | 0.44 | 0.44 | 0.88 | 1.65 | — | 1.65 |
| TDC-20 Complex | — | — | — | — | — | — | — | — | — | — | — | — | — | 5.0 | — |
| Sodium Iodate | 0.3 | 0.3 | 0.3 | 0.3 | 0.3 | 0.3 | 0.3 | 0.3 | 0.3 | 0.3 | — | — | — | — | 0.5 |
| Citric Acid | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 |
| Aerosol OT-75 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Sodium Hydroxide | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Methocel E4M Premium | — | — | — | — | — | — | — | — | — | 0.1 | — | — | — | — | — |
| Methocel E10M Premium | — | — | — | — | — | — | — | — | — | — | — | — | — | — | — |
| Rheothik 80-11 | — | — | — | — | — | 8.0 | 8.0 | — | — | — | — | — | — | — | — |
| Keltrol | 0.2 | 0.1 | 0.1 | 0.2 | 0.2 | — | 0.2 | 0.2 | 0.2 | 0.2 | 0.2 | 0.2 | 0.2 | 0.2 | 0.2 |
| Glycerin | 10.0 | — | 10.0 | — | 10.0 | 10.0 | 10.0 | 10.0 | 10.0 | 10.0 | 10.0 | 10.0 | 10.0 | 10.0 | 10.0 |
| Propylene Glycol | — | 10.0 | — | 10.0 | — | — | — | — | — | — | — | — | — | — | — |
| Water | q.s. | q.s. | q.s. | q.s. | q.s. | q.s. | q.s. | q.s. | q.s. | q.s. | q.s. | q.s. | q.s. | q.s. | q.s. |
| Brookfield Viscosity (CP, Spindle #2, 6 RPM) | 450 | 100 | 100 | 400 | 350 | 125 | 725 | 435 | 450 | 375 | 450 | 450 | 375 | 1000 | 375 |

Compositions 1–3 contained 1% iodine complexed with 2% PVP K-90 and 0.5% Pluronic P-105. A combination of hydroxypropyl methyl cellulose (Methocel E10M Premium) and xanthan gum (Keltrol) were used as the thickening agents. Glycerin and propylene glycol were used as conditioning agents. The formulations gave films that were somewhat tacky and stringy.

Compositions 4–6 are similar to compositions 1–3, except that 2% Pluronic P-105 was used, and a lower molecular weight cellulose thickener (Methocel E4M Premium) was used. These formulations gave a dryer, waxier film which were slightly stringy. Compositions 7–11 were similar to the foregoing, except that PVP K-30 was used. The resultant films did not exhibit the stringy nature of the earlier K-90 compositions.

Compositions 12–19 contained either 0.5% or 2% Pluronic P-105, PVP K-30, and Keltrol as a thickener. Samples with 2% P-105 were less tacky and waxier than those with 0.5% P-105.

Compositions 20–21 contained 2% PVP K-30, 2% Pluronic P-105 and a poly(sulfonic acid) thickening agent (Rheothik 80-11). The resultant films were soft and sticky.

Compositions 22–25 contained 0.25% iodine and various levels of Pluronic P-105. Higher levels of P-105 gave films that were waxier and less tacky.

Composition 26 contained 0.5% iodine but is otherwise identical to composition 25. This gave a essentially equivalent film.

Compositions 27–28 contained 2% Pluronic P-123 and 6% nonylphenol ethoxylate (Igepal CO-720), respectively. The P-123 sample gave a soft waxy film whereas the Igepal CO-720 product gave an oily, non-uniform film.

Composition 29 contained a higher level of iodate which provides a stable, higher concentration of free iodine.

As a comparison, a composition was prepared as set forth above containing the following ingredients: 50% solution of sodium hydroxide, 0.33% by weight; Igepal CO-720, 6.0% by weight; sodium iodide, 0.16% by weight; citric acid, 0.25% by weight; TDC-20 complex, 5.0% by weight; glycerin, 10.0% by weight; and water, q.s. to 100% by weight. This comparative composition exhibited a viscosity of less than 20 cP, and was not satisfactory in accordance with the invention, in that it did not give the desired film of conditioning agent.

EXAMPLE 2

Two preferred film-forming teat dips in accordance with the invention were prepared, and compared to existing iodine-based teat dips.

The film-forming dips contained the following ingredients on a percent by weight basis:

Composition 30—PVP K-30, 2.0%; Pluronic P-105, 2.0%; NaI-I$_2$ Complex, 1.65%; sodium iodate, 0.5%; citric acid, 0.3%; Aerosol OT-75, 0.05%; sodium hydroxide (50%), 0.1%; glycerin, 10.0%; Keltrol, 0.2%; and water, q.s. 100%.

Composition 31—PVP K-30, 2.0%; Pluronic P-105, 2.0%; NaI-I$_2$ Complex, 1.65%; sodium iodate, 0.5%; citric acid, 0.3%; Aerosol OT-75, 0.05%; sodium hydroxide (50%), 0.1%; glycerin, 6.0%; propylene glycol, 4.0%; Keltrol, 0.2%; and water, q.s. 100%.

These two dips were compared to two commercial liquid-type dips, namely Bovadine®-ACT™ commercialized by West Agro, Inc. of Kansas City, Mo., and Mastimin® Plus commercialized by Diversey Corporation of Livonia, Mich. In particular, the four dips were tested to determine their film-forming characteristics. In each case, twenty-five 16 mm diameter glass culture tubes were initially weighed and dipped in the particular teat dip to a depth of 6½ to 7 cm. After dipping, the 25 tubes were allowed to drain for 1 to 1½ minutes and were weighed to provide a wet weight. The tubes were then allowed to dry in ambient air for a period of 45 minutes, whereupon the tubes were reweighed to provide a dry weight. The following table sets forth the results of this test.

TABLE 2

| Teat Dip | Average Wet Weight/Tube (mg.) | Average Dry Weight/Tube (mg.) |
| --- | --- | --- |
| Composition 30 | 316 | 52 |
| Composition 31 | 260 | 52 |
| Bovadine ®-ACT ™ | 132 | 20 |
| Mastimin ® Plus | 40 | 12 |

As can be seen, the products of the invention had substantially higher dry weights as compared with the conventional products, thereby establishing the film-forming capabilities thereof. In this connection, experience with the compositions of the invention demonstrates that the resultant films are of a soft, waxy nature, as compared with prior "barrier" dips which tend to leave a more rigid type of film. These prior barrier dips are deficient in that the residual films they leave are relatively dry and can be peeled from the teats. By comparison, the soft, waxy films of the present compositions do not dry to this extent, and are thus resistant to removal by abrasion. Additionally, the products of the invention provide residual films that are comprised primarily of conditioning agents which maximize skin conditioning properties.

The ingredients used for the preparation of teat dip compositions in the foregoing examples are for the most part commercially available. The iodine sources used include a sodium iodide-iodine complex having average titratable iodine value of 56.2–58% by weight, a total iodides of from 76.0–78.5% by weight, and an iodide content as iodide ion of 19.0–22.0% by weight. Another source was the TDC-20 product which is iodine complexed with Igepal CO-720. This product contained a titratable iodine value of 21.0–21.3% by weight (at the time of manufacture), and a total iodides content of about 26.25%.

The preferred surfactant complexors used in these examples included Igepal CO-720 (nonoxynol 12) which is a nonionic surfactant of the nonylphenoxypoly(ethyleneoxy) ethanol type. The Igepal CO-720 product has CAS #9016-45-9. Pluronic P-105 (Poloxamer 335) and Pluronic P-123 (Poloxamer 403) are nonionic polyoxyethylene-polyoxypropylene block copolymers, CAS #9003-11-6.

The thickeners included Keltrol which is a xanthan gum in the form of a high molecular weight natural polysaccharide, CAS #11138-66-2. The Methocel products are hydroxypropyl methylcellulose thickeners made using propylene oxide and methylchloride. Methocel E10M Premium and Methocel E4M Premium each have CAS #9004-65-3. The Rheothik 80-11 thickener is a polyorgano sulfonic acid, CAS #27119-07-9. The preferred PVP product K-30 has CAS #9003-39-8.

The wetting agent employed in the exemplary compositions, Aerosol OT-75 is sodium dioctyl sulfosuccinate in a mixture of ethanol and water (CAS #577-11-7 and 53023-94-2).

As can be seen from the foregoing examples, film-forming teat dips in accordance with the invention may include a variety of ingredients at varying levels. The following table summarizes the ingredients used in the dips in percent by weight.

TABLE 3

| Ingredient | Broad Range | Preferred Range |
| --- | --- | --- |
| Germicidal Agent | 0.05–5 | 0.1–1.5 |
| Thickener(s) | 0.05–10 | 0.1–1 |
| Polyvinyl Pyrrolidone | 0.5–5 | 1.0–2.5 |
| Conditioning Agent(s) | 0.5–20 | 2.0–10 |
| Complexing Agent | 0.4–10 | 0.4–4 |
| Water | q.s. 100% | q.s. 100% |

We claim:

1. A topical germicide consisting essentially of an aqueous composition including a germicidal agent selected from the group consisting of iodine and chlorhexidene, a thickener, from about 0.5–20% by weight of a skin conditioning agent selected from the group consisting of glycerin and propylene glycol and mixtures thereof, and an amount of polyvinyl pyrrolidone, said composition having a viscosity of from about 50–5000 cP and characterized by the property of leaving a residual film when applied to skin.

2. The germicide of claim 1, said germicidal agent being iodine.

3. The germicide of claim 2, said complexed iodine comprising iodine and a complexing agent selected from the group consisting of ethoxylated surfactants, cellulose, the celluloses and said polyvinyl pyrrolidone.

4. The germicide of claim 3, said ethoxylated surfactants being selected from the group consisting of alkylphenol ethoxylates, ethoxylated fatty acids, alcohol ethoxylates, alcohol alkoxylates, polysorbates (ethoxylated sorbitol) and ethylene oxide-propylene oxide copolymers.

5. The germicide of claim 4, said surfactant being an ethylene oxide-propylene oxide copolymer.

6. The germicide of claim 1, said germicidal agent being iodine, said iodine being present at a level of from about 0.1–2% average available iodine on a nominal basis.

7. The germicide of claim 6, said level being from about 0.25–1%.

8. The germicide of claim 1, said polyvinyl pyrrolidone having a molecular weight of from about 10,000–150,000.

9. The germicide of claim 8, said molecular weight being from about 25,000–90,000.

10. The germicide of claim 1, said thickener being selected from the group consisting of cellulose, the celluloses and gums.

11. The germicide of claim 10, said thickener being selected from the group consisting of the alkyl celluloses, the alkoxy celluloses, xanthan gum, guar gum, polyorgano sulfonic acid and mixtures thereof.

12. The germicide of claim 1, said thickener being present in said composition at a level of from about 0.05–10% by weight.

13. The germicide of claim 12, said level being from about 0.1–1% by weight.

14. The germicide of claim 1, said polyvinyl pyrrolidone being present at a level of from about 0.5–5% by weight.

15. The germicide of claim 14, said level being from about 1–2.5% by weight.

16. The germicide of claim 1, said viscosity being from about 100–1000 cP.

17. The germicide of claim 1, said conditioning agent being present in an amount from about 2.0–10% by weight.

18. The germicide of claim 1, including from about 0.1–0.6% by weight of iodate ion.

19. The germicide of claim 1, including a buffering agent.

20. The germicide of claim 1, said germicidal agent being complexed iodine, the weight ratio of complexor agent to iodine being from about 2:1 to 4.5:1.

21. The germicide of claim 1, said germicide being formulated as a teat dip and containing a germicidal agent effective for the prevention of bovine mastitis.

22. A method of treating bovine teats comprising the step of dipping said teats in a composition in accordance with claim 21, and allowing the composition to dry and form a residual film on said teats.

* * * * *